United States Patent [19]
Bezier

[11] Patent Number: 5,731,061
[45] Date of Patent: Mar. 24, 1998

[54] PERFORATED THERMOPLASTIC SHEET IN WHICH THE PERFORATION CRATERS HAVE SIDEWALLS THAT PRESENT CONVERGING PORTIONS AND DIVERGING PORTIONS, A FIBROUS COMPOSITE PLANE MATERIAL INCLUDING SUCH A SHEET, AND METHODS OF MANUFACTURE

[75] Inventor: Bernard Bezier, Lambersart, France

[73] Assignee: Guial S.A., France

[21] Appl. No.: 615,221

[22] PCT Filed: Jul. 7, 1995

[86] PCT No.: PCT/FR95/00915

§ 371 Date: Mar. 14, 1996

§ 102(e) Date: Mar. 14, 1996

[87] PCT Pub. No.: WO96/02215

PCT Pub. Date: Feb. 1, 1996

[30] Foreign Application Priority Data

Jul. 15, 1994 [FR] France ................... 94 09009
Aug. 11, 1994 [FR] France ................... 94 10092

[51] Int. Cl.[6] .................................... A61F 13/15
[52] U.S. Cl. .......................... 428/131; 428/132; 428/137; 428/134; 604/385.1; 442/394; 442/399; 442/398; 264/504; 264/511; 264/571
[58] Field of Search ......................... 428/131, 132, 428/137, 134; 604/385.1; 442/394, 399, 398; 264/504, 511, 571

[56] References Cited

U.S. PATENT DOCUMENTS

| | | | |
|---|---|---|---|
| H1575 | 8/1996 | Daugherty et al. | 428/284 |
| H1579 | 8/1996 | Furio | 502/402 |
| 3,929,135 | 12/1975 | Thompson | 128/287 |
| 4,324,246 | 4/1982 | Mullane et al. | 128/287 |
| 4,342,314 | 8/1982 | Radel et al. | 128/287 |
| 5,171,238 | 12/1992 | Kajander | 604/383 |
| 5,567,376 | 10/1996 | Turi et al. | 264/455 |
| 5,614,283 | 3/1997 | Potnis et al. | 428/131 |

FOREIGN PATENT DOCUMENTS

| | | |
|---|---|---|
| 0156471 | 10/1985 | European Pat. Off. . |
| 0302611 | 2/1989 | European Pat. Off. . |
| 0532937 | 3/1993 | European Pat. Off. . |
| 0545423 | 6/1993 | European Pat. Off. . |
| 9309741 | 5/1993 | WIPO . |
| 9312749 | 7/1993 | WIPO . |

*Primary Examiner*—Kathleen Choi
*Attorney, Agent, or Firm*—Ladas & Parry

[57] ABSTRACT

The perforated sheet, in particular for sanitary articles, and made of a substance that is impervious to liquid, includes a multiplicity of craters each having a base in the plane of the outside face, an apex, and a sidewall that slopes between the base and the apex. The peripheral shape of the base includes at least one zone of discontinuity such that on going round the periphery of each crater, its sidewall presents non-uniform inclination with angles of inclination relative to the perpendicular to the plane of the outside face of the sheet that vary between positive values and negative values, said angle being negative at least in the zone of discontinuity. The peripheral shape of the base is preferably the result of partially overlapping a plurality of curved geometrical shapes, in particular circles and ellipses, and the zone of discontinuity corresponds to the junction between superposed shapes. The composite plane material includes said sheet covered in thermoplastic fibers on at least its outside face, which fibers are bonded to one another and to the sheet.

17 Claims, 3 Drawing Sheets

5,731,061

PERFORATED THERMOPLASTIC SHEET IN WHICH THE PERFORATION CRATERS HAVE SIDEWALLS THAT PRESENT CONVERGING PORTIONS AND DIVERGING PORTIONS, A FIBROUS COMPOSITE PLANE MATERIAL INCLUDING SUCH A SHEET, AND METHODS OF MANUFACTURE

The present invention relates to a perforated thermoplastic sheet made in a material that is impervious to liquids and used, in particular, as a protective covering for an absorbent body, e.g. in the field of sanitary articles such as disposable diapers or nappies and sanitary napkins or towels.

BACKGROUND OF THE INVENTION

In this type of sanitary article, the absorbent wad is generally sandwiched between an outer sheet that is impervious to liquids, thereby avoiding wetting the user's clothing, and an inner protective sheet which is in contact with the skin of the user. The protective sheet must allow the liquid discharged by the user to pass through while ensuring a degree of comfort.

Proposals have already been made in document FR 2 294 656 for a disposable diaper in which the protective sheet is made of a material that is impervious to liquids and that has convergent orifices or capillaries with openings of sizes that are critical and with convergence angles that are likewise critical, the absorbent element being in intimate contact with the apexes of said convergent capillaries. The convergence angle of the capillaries is about 10° to about 60°. Each capillary has a base in the outer plane of the protective sheet, the size of the opening of said base is about 0.15 mm to 6.35 mm, while the size of the opening at the apex of each capillary is about 0.1 mm to 2.54 mm.

According to the teaching given in that prior document, the above-mentioned convergence and sizes allow liquid to pass from the outer surface of the protective sheet towards the absorbent body, while guaranteeing that there is no flow of liquid in the opposite direction. The convergent capillaries formed in the protective sheet act somewhat like non-return valves.

OBJECTS AND SUMMARY OF THE INVENTION

The object of the Applicant is to propose a perforated thermoplastic sheet which can be used as a protective sheet for sanitary articles and which, in known manner, includes sorts of capillaries enabling liquid to pass through the sheet while acting as non-return valves, but without being restricted as to the sizes of said capillaries.

Such a perforated sheet is made of a material that is impervious to liquids and it includes a multiplicity of craters, each having a base in the plane of the outer face of the sheet, an apex remote from said plane, and a sidewall which is inclined going from the base to the apex of the crater.

In a manner characteristic of the invention, the base of each crater has a peripheral shape including at least one zone of discontinuity, i.e., inward contraction of the peripheral curve of the crater, such that on going round the periphery of each crater, the sidewall presents an inclination that is not uniform, having angles of inclination relative to the perpendicular to the plane of the outside face of the sheet varying between positive values and negative values, said angle being negative at least in the zone of discontinuity.

For comparison with the teaching of prior document FR 2 294 656, a positive angle of inclination for the sidewall corresponds to a converging profile while a negative angle corresponds to a diverging profile. Thus, because of the presence of the zone of discontinuity and because of the particular inclination of the sidewall in said zone, it has been possible for the Applicant, surprisingly, to provide a perforated thermoplastic sheet of the invention with craters of sizes that are not restricted, while nevertheless preserving their functions of transferring liquid and of acting as a non-return valve.

Preferably, the peripheral shape of the base of the crater is the result of partially overlapping a plurality of curved geometrical shapes, in particular circles and ellipses, and the zone of discontinuity corresponds to the junction between overlapping shapes.

In a preferred embodiment, the base of each crater has a curved outline with a longitudinal axis of symmetry (EE') that is the result of partially overlapping an ellipse with at least one circle whose center lies on the longitudinal axis of the ellipse. In a first variant, there is partial overlap of an ellipse and a single circle; in a second variant, there is partial overlap of an ellipse and two circles disposed at opposite ends of the ellipse. In the second variant, the base of each crater has four zones of discontinuity corresponding to the junctions between the substantially elliptical central portion and the two substantially circular end portions.

Preferably, in both of the above-mentioned variants, the length of each crater along its longitudinal axis L of symmetry lies in the range 2.6 mm to 4 mm whereas the diameter of the end circle(s) lies in the range 0.6 mm to 3 mm.

Advantageously, the thermoplastic sheet of the invention includes a plurality of types of crater alignment, the craters in the same type of alignment being regularly aligned along a common longitudinal axis of symmetry, with alignments of the same type having the same general direction.

Preferably, the sheet has four types of alignment, whose general directions are mutually angularly offset through angles of 45°. Because of this particular disposition, the sheet offers uniform strength in a dynamometer, without any privileged deformation.

Advantageously, when the base of the crater comprises at least one zone of narrowing extending between two zones of discontinuity, each crater includes in said zone of narrowing, a fibril element forming a spacer between the two sidewalls of the crater that face each other in this zone of narrowing and that correspond to the zones of discontinuity. The presence of the fibril element serves to increase the strength of the sheet in a dynamometer, particularly when the craters are of large sizes.

Another object of the invention is to propose a perforated thermoplastic sheet as specified above, which also has improved "feel". This is obtained by means of the composite plane material which is made up of such a perforated thermoplastic sheet together with fibers covering at least the smooth outer face of said sheet and which are bonded to one another and to the sheet in a manner that is substantially continuous.

Preferably, the fibers are bonded to one another and to the sheet, including over the sidewalls of the craters.

When fibril elements exist forming spacers between the two sidewalls that face each other in the zones of narrowing of the craters, corresponding to the zones of discontinuity, the fibers are preferably bonded to one another and to the fibril elements.

When contact is made with the skin of the user, the presence of fibers at the surface of the thermoplastic sheet, on its outside face, gives the material of the invention a fibrous feel which is more agreeable.

In a first version, the fibers are bonded to one another and to the sheet solely by means of the thermoplasticity of the substances from which they are made. In which case, it is preferable for the majority of the fibers to be thermoplastic fibers so that the composite material of the invention has sufficient cohesion between the sheet and the fibers.

Preferably, the thermoplastic fibers and the sheet are made of the same substance, e.g. polyethylene. However, the sheet may be made of some other substance such as polyamide or polypropylene, or a mixture of polyolefins. The thermoplastics fibers may be made of polypropylene.

In a second version, the fibers are bonded to one another and to the sheet by the presence of adhesive, preferably in combination with the thermoplasticity of the substance from which the sheet and the fibers are made. In this case, it is possible to use substances having significantly different melting points.

The quantity of adhesive must be relatively small so as to avoid spoiling the flexibility of the composite material. The quantity of adhesive is preferably in the range 0.2 grams per square meter (g/m$^2$) to 5 g/m$^2$ for a quantity of fibers in the range 2 g/m$^2$ to 20 g/m$^2$.

Another object of the invention is to propose a method of manufacturing the above-specified fibrous composite plane material. The method consists:

a) in dispersing a web of fibers, the majority of which are thermoplastic fibers, on a thermoplastic sheet, optionally pre-coated in adhesive;

b) in presenting the sheet/fiber assembly thus obtained on a surface that is provided with orifices, the peripheral shape of each orifice being the result of partially overlapping a plurality of curved geometrical shapes, in particular circles or ellipses; and c) in heating said assembly to a temperature close to the softening temperature of the thermoplastic substances constituting the fibers and the sheet while simultaneously establishing suction through the orifices so as to obtain craters by bursting the sheet where it overlies the orifices, each crater having a base whose peripheral shape includes at least one zone of discontinuity such that on going round the periphery of each crater, the sidewall of the crater has non-uniform inclination with angles of inclination relative to the perpendicular to the plane of the outside face of the sheet that vary between positive values and negative values, said angle being negative at least in the zone of discontinuity.

Heating the sheet/fiber assembly serves simultaneously to soften the thermoplastic sheet in the zone corresponding to the orifices and also to bond the fibers to one another and to the sheet at the points of contact between these various constituent parts. In particular, it is observed that the walls of the craters formed during bursting of the sheet under the effect of suction through the orifices constitute privileged bonding zones between the fibers and the sheet.

The fibers are dispersed in the form of a web on the surface of the thermoplastic sheet by any appropriate means, in particular by blowing on fibers using the cut fiber or "spun" technique, or using the "melt-blown" technique.

In a preferred version, the manufacturing method is a continuous method and the surface on which the sheet/fiber assembly is presented is constituted by the peripheral surface of a rotary drum fitted with an internal suction system.

The sheet/fiber assembly can be heated, in particular, by means of radiant panels disposed above the surface of the drum over the portion thereof which is fitted with the suction system.

A fibrous composite plane material of the invention can also be obtained by means of another method whereby a web of thermoplastic fibers is dispersed over a perforated thermoplastic sheet having a multiplicity of craters each with a zone of discontinuity, as described above, fiber dispersion being performed over at least the smooth outside face of the sheet, with fibers that are at a temperature which is sufficient for them to adhere naturally to the surface of the sheet after it has cooled.

In this case, the sheet is uniformly covered by the web of fibers and the fibers are spot-bonded to one another and to the sheet solely by the thermoplasticity of the materials, engaging the surface of the sheet and excluding its craters.

To be certain that the fibers hold together and to the surface of the sheet, a variant of the above-specified method consists in pre-coating the smooth face of the thermoplastic sheet with adhesive that withstands said temperature. The adhesive is preferably likewise a thermoplastic polymer, suitable for use in the melt-blown technique.

BRIEF DESCRIPTION OF THE DRAWINGS

The present invention will be better understood on reading the following description of embodiments of a perforated sheet having a multiplicity of oblong-shaped craters with one or two successive narrowings, as illustrated in the accompanying drawings, in which.

MORE DETAILED DESCRIPTION

The perforated thermoplastic sheet described below is designed to be included in an absorbent structure suitable for use as a sanitary article, e.g. a diaper or a sanitary napkin. Naturally it can be used in other applications where advantage can be taken of its properties of transferring liquids in one direction with a non-return effect in the opposite direction.

In all such articles, the absorbent cushion which is generally made of cellulose wadding, is protected on the outside by a sheet that is impervious to liquid and on the inside by a protective sheet. The protective sheet must allow liquid to pass through, whether the liquid is urine or blood, so as to enable it to be absorbed by the absorbent cushion, and it must also provide comfort to the user. In particular, proposals have already been made for said protective sheet to be made of a substance that is impervious to liquid, e.g. polyethylene, but that includes perforations in the form of convergent capillaries, preferably of frustoconical shape, having an angle of convergence and sizes that are determined in such a manner that the liquid can pass through said sheet in one direction while preventing it from flowing back in the opposite direction. The apexes of the convergent capillaries are in close contact with the absorbent cushion.

One such perforated sheet is described in document FR 2 294 656. The angle of convergence of the capillaries ties in the range 10° to 60°; the size of the opening of a capillary at its base in the outer plane of the sheet is about 0.15 mm to 6.35 mm while the size of the opening at the apex is about 0.1 mm to 2.54 mm.

Figure 1:
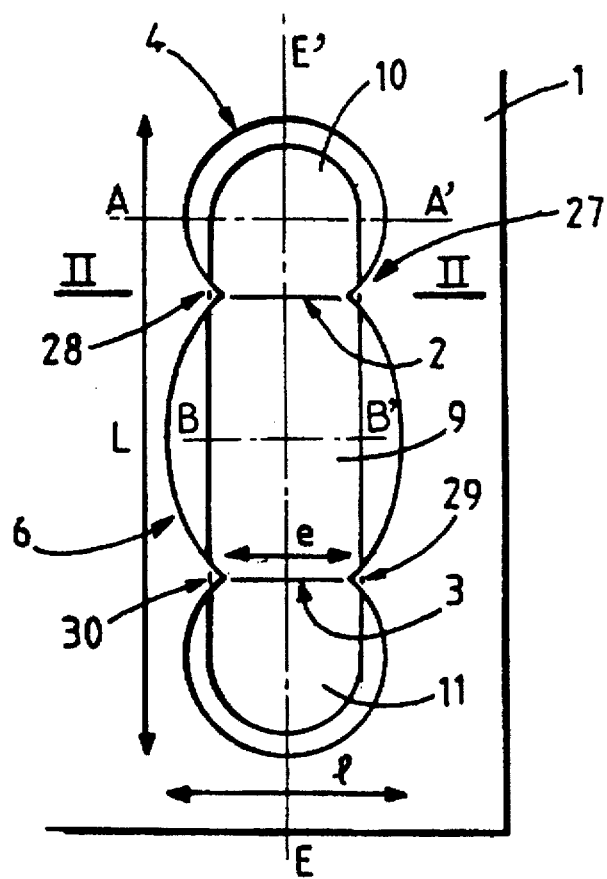
FIG. 1 is a diagrammatic plan view of a portion of the sheet having a crater with two successive narrowings.

The sheet 1 of the present invention, as shown in FIG. 1, is made of a thermoplastic material that is impervious to liquid, in particular polyethylene, and it has a multitude of perforations or craters 6, each of which is elongate in shape having a length L and a maximum width l. The base 4 of each crater 6 has four zones of discontinuity 27, 28, 29, and 30 which face each other in pairs, so as to define two zones of narrowing 2 and 3. In addition, the sidewall which extends from the base 4 to the apex 5 of the crater 6 has an inclination that is non-uniform around the periphery of the crater. With reference to the perpendicular DD' to the plane PP' including the outside face of the sheet 1, the angle of inclination α of the sidewall varies, on going round the entire periphery of the crater 6, through values that are positive and values that are negative. A positive value for the angle α means inclinations of the convergent type as shown in document FR 2 294 656. A negative value for the angle α means inclinations of the divergent type.

Figure 2:
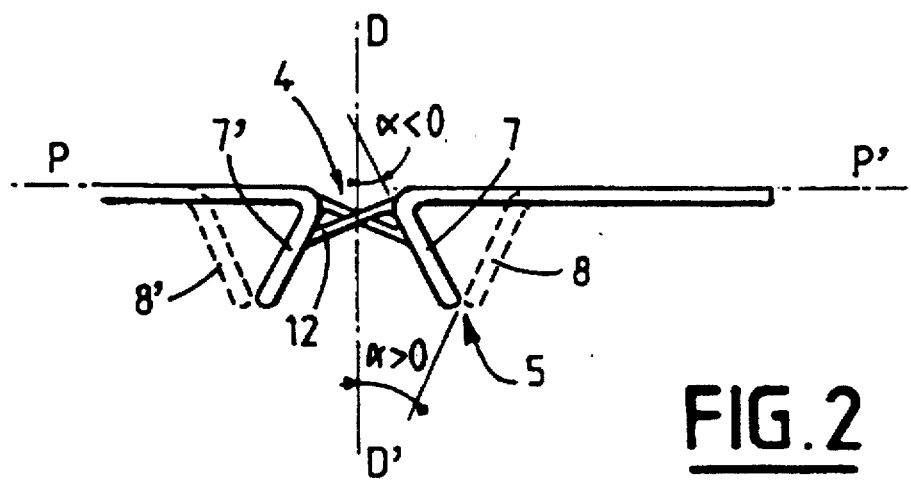
FIG. 2 is a diagrammatic section view of the sheet on axis II—II.

More precisely, the angle of inclination α has negative values in the zones of discontinuity 27 and 30 that correspond to the zones 2 and 3 of narrowing. In FIG. 2, the solid line is a section through the sheet 1 of FIG. 1 in a zone 2 of narrowing where the walls 7 and 7' of the crater 6 have a negative angle α whereas the dashed line is a section through the sheet 1 in a zone without narrowing, on axis AA' in FIG. 1, where the angle of inclination of the sidewalls 8 and 8' is positive.

Thus, on examining the shape of the base 4 of the crater 6 shown in FIG. 1, the configuration of the base is substantially that of an ellipse in its central portion 9 and substantially that of two circles in its end portions 10 and 11, said two circles 10 and 11 and the ellipse 9 overlapping in part so as to have zones in common which correspond to the zones of narrowing 2, 3.

A crater of this type can be obtained in a sheet of thermoplastic material by means of the method described in document U.S. Pat. No. 3,054,148. In this method, the sheet is applied to a surface that has orifices, e.g. on a perforated rotary drum, the sheet is raised to a temperature close to its softening temperature, e.g. by blowing hot air, and suction is established through the orifices so as to cause the sheet to burst where it overlies said orifices.

In the present invention, the orifices have the shape described above for the base 4 of the crater 6.

During suction, the portion of the sheet that overlies the orifice deforms so as to penetrate inside the orifice in the form of a kind of bubble which, on bursting, forms the sidewall of the crater 6.

Because of the special shape of the orifice and the zones of narrowing 2 and 3, the sidewall is not uniform in profile but presents non-uniform inclination having both positive and negative angles, as explained above.

It is because of these features that it is possible to make craters 6 without restrictions on the length L, while nevertheless maintaining the characteristics of the crater, i.e. passing liquid and the non-return effect.

Naturally the invention is not limited to the configuration shown in FIG. 1, and many other configurations can be implemented providing they have at least one zone of discontinuity so that on going round the periphery of each crater, the sidewall has non-uniform inclination with angles of inclination relative to the perpendicular to the plane of the outside face of the sheet the vary between positive values and negative values, the angle being negative at least in the zone of discontinuity. In particular, the peripheral shape of the base of the crater may be the result of partially overlapping curved geometrical shapes such as circles or ellipses, such that the zone(s) of discontinuity correspond to junctions between the overlapping shapes. In the example above, there are one ellipse and two circles, sharing a common longitudinal axis and disposed at opposite ends of the ellipse, but other combinations are possible: two circles of the same diameter or of different diameters, two ellipses that are identical or different; one ellipse and a single circle, . . . with any partial overlap between at least two curved geometrical shapes, whether they are of the same kind or of different kinds, of the same size or of different sizes, making it possible to define one or more zones of discontinuity at the junction(s) therebetween.

Depending on the type of thermoplastic material used for making the sheet 1, and also as a function of the width e of the base 4 in the zone of discontinuity, filamentary elements 12 may be formed between the walls 7 and 7' of the crater 6 when implementing the manufacturing method described in document U.S. Pat. No. 3,054,148. These filamentary elements constitute a residual link between the walls 7 and 7', in this case between two zones of discontinuity 27 and 28, and they contribute to reinforcing the dynamometer strength of the sheet 1 in the transverse direction. They are the result of partially melted portions of the substance from which the sheet is made, after bursting.

Figure 3:
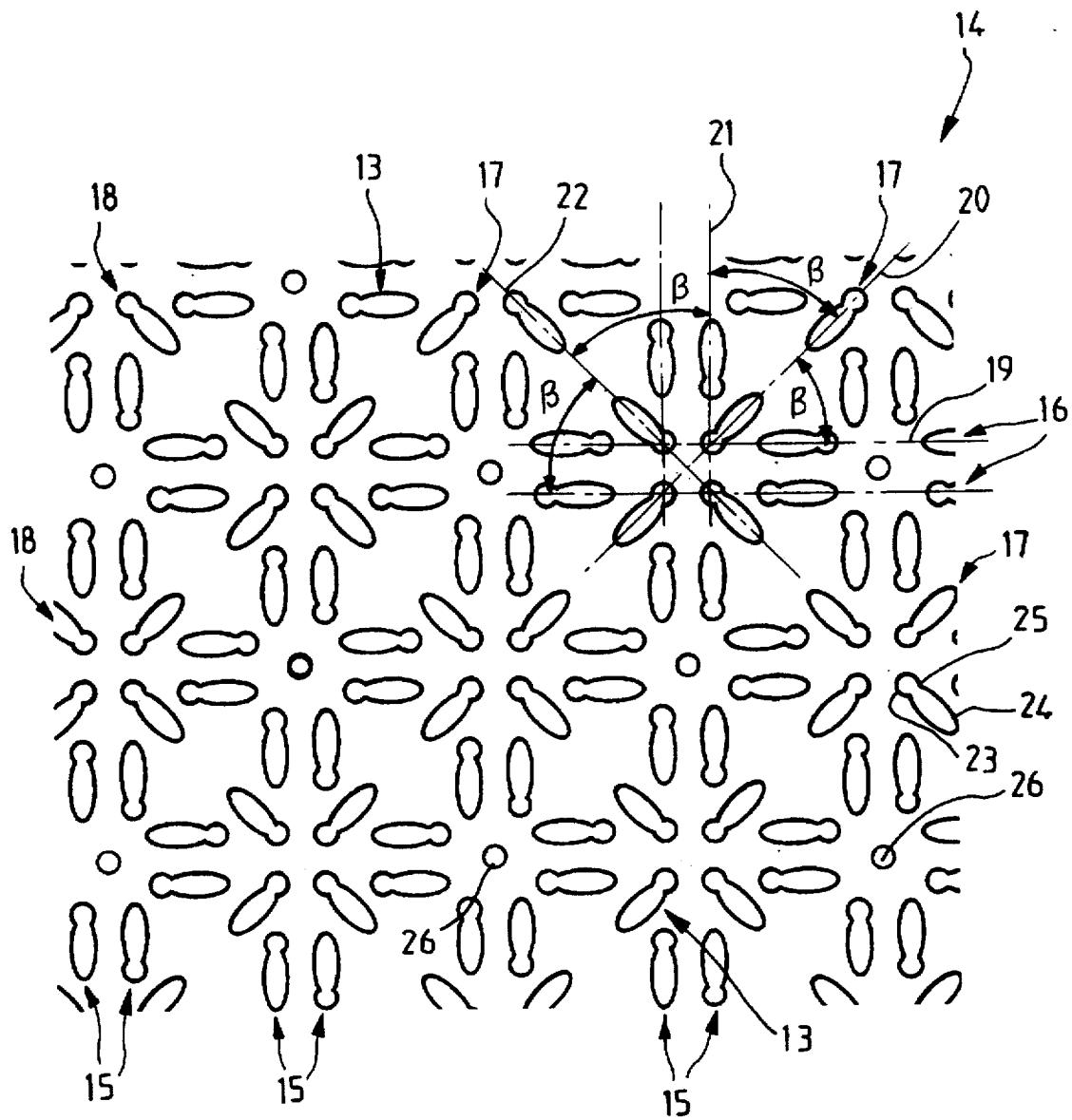
FIG. 3 is a diagrammatic plan view of a sheet showing the disposition of four types of alignment of craters each having a single narrowing.

FIG. 3 is a highly diagrammatic representation of a preferred disposition for craters in a sheet 14. In this disposition, the craters 13 are distributed along four types of alignment. The term "alignment" is used to mean a succession of craters 13 sharing a common longitudinal axis of symmetry. In the example shown in FIG. 3, each crater 13 has a base that is the result of partially overlapping an ellipse and a circle. A given type of alignment consists in a plurality of alignments of craters 13 having the same general direction. The sheet 14 of FIG. 3 thus has four types of alignment 15, 16, 17, and 18 having four different general directions 19, 20, 21, and 22 respectively which are mutually offset by angles β equal to 45°. Because of this particular disposition, in four types of alignment that are regularly distributed angularly, a sheet 14 is obtained having dynamometer properties that are entirely uniform without any privileged deformation.

As can be seen in FIG. 3, in a given alignment, the craters 13 may be oriented in the same direction or their orientation may alternate from one crater 13 to the next. This concept of orientation exists when the craters 13 are not symmetrical about an axis extending transversely to the geometrical shape of the crater. For the crater 6 shown in FIG. 1, the two circular end portions 10 and 11 are symmetrical about the transverse axis BB' through the central elliptical portion 9. However this does not apply to the crater 13 of FIG. 3, and orientation depends on the positions of the circular portions 23 relative to the elliptical portions 24.

In addition, the sheet 14 may also have a small number of circular craters 26, additional to the craters 13 having a zone of narrowing 25.

The invention is not limited to the embodiment described above. It will be understood that the advantage provided by the special shape of the craters lies in the possibility of greatly increasing the open fraction of area that allows liquid to pass through, thereby obtaining a greater liquid absorption capacity for the absorbent cushion, while not reducing the non-return effect. This improves user comfort substantially.

Figure 4:
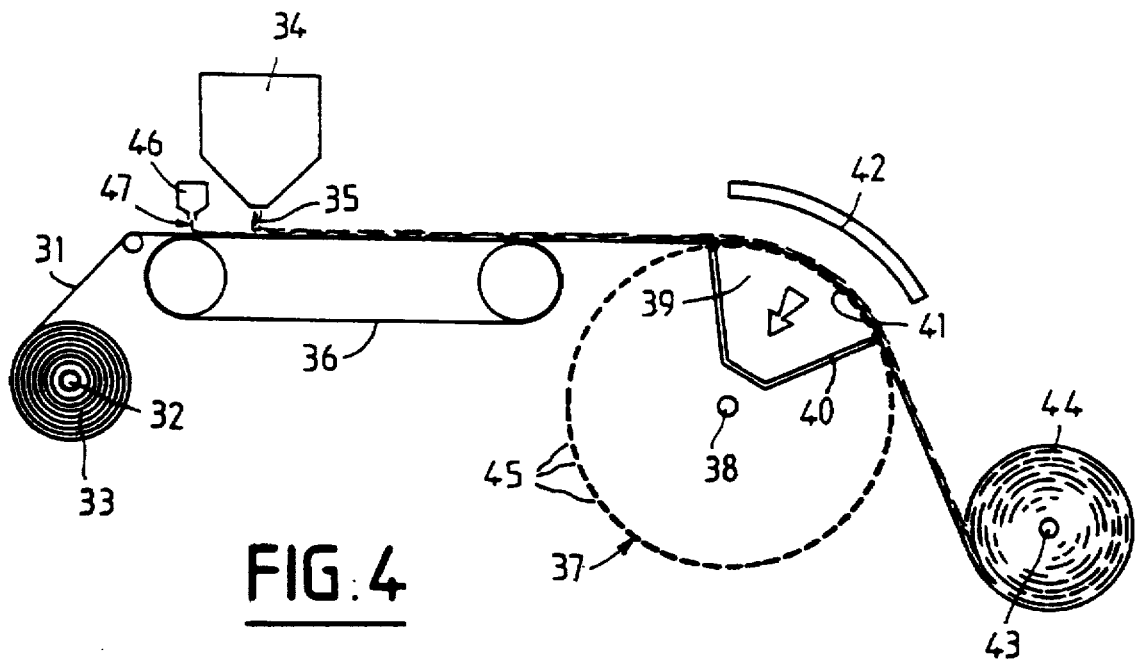
FIG. 4 is a diagram of the installation for manufacturing a fibrous composite material including the perforated sheet.

The perforated sheet of the invention may advantageously be implemented in a fibrous composite material, and FIG. 4 shows an installation for manufacturing it.

The installation has means for feeding a thermoplastic sheet 31, e.g. a polyethylene sheet. These means may comprise a shaft 32 rotated by drive means (not shown) and having a roll 33 fitted thereon made up of rolled-up sheet 31.

On the path of said sheet 31, the installation includes a device 34 for blowing on fibers 35, which device is disposed above a conveyor 36 suitable for supporting the sheet 31 during this operation of making a web of fibers 35 on the top face of said sheet 31.

The installation also includes a rotary drum 37 that rotates about an axis 38 and that is driven by known means (not shown). The periphery of the drum has a multiplicity of orifices 45 of a shape that corresponds to that described above for the base 4 of the crater 6.

The drum 37 is a hollow cylinder having a suction chamber 39 disposed inside it. The chamber 39 is substantially airtight and is defined by a sidewall 40 which is stationary and by a portion 41 of the drum 37. Known suction means communicate with the chamber 39, e.g. a fan.

The installation also includes a set of radiant panels 42 disposed in a circular arc over the portion of the drum 37 facing the suction chamber 39.

Finally, the installation includes means 43 for taking up the composite material The installation operates as follows. The thermoplastic sheet 31 is placed on the conveyor 36. The device 34 blows a continuous and regular web of fibers 35 onto the top face of the sheet 31, the fibers being merely placed on the sheet 31 without any particular bonding thereto.

The assembly constituted by the sheet 31 and the web of fibers 35 is conveyed to the drum 37 and is pressed thereagainst substantially over the entire portion 41 facing the suction chamber 39 prior to being wound onto the take-up device 43. While the sheet/fiber assembly is moving on the drum 37 as the drum rotates about its axis 38, it is subjected simultaneously to the heating action of the radiant panels 42 and to the suction action of the chamber 39.

The effect of the heating action is to raise the sheet/fiber assembly to a temperature close to the softening temperature of the thermoplastic substances constituting the sheet 31 and the fibers 35.

Because of the orifices 45 present in the drum 37, the suction action has the effect not only of holding the sheet 31 on the surface of said drum 37, but also of creating perforations through the sheet/fiber assembly. Since the thermoplastic sheet 31 is in a state close to softening, the suction forces deform those areas of the sheet that overlie the orifices 45; this deformation which is similar to blistering, leads to bursting, thus forming a crater 6. The sheet 31 is thus pierced merely under the mechanical action due to suction.

Figure 5:
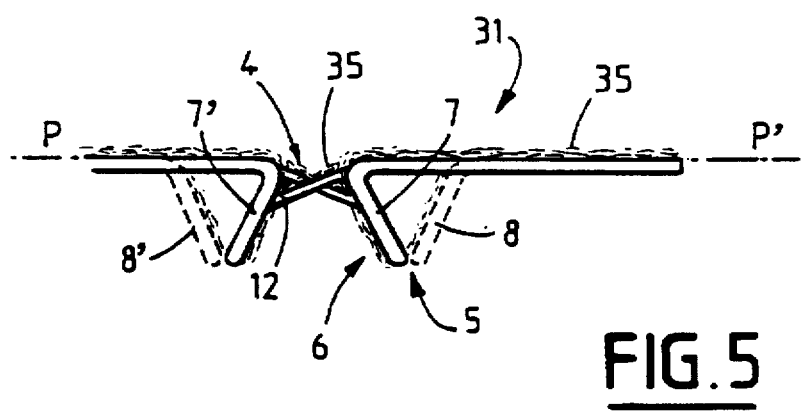
FIG. 5 is a diagrammatic section view through the composite material that includes the perforated sheet of FIG. 2.

The fibers 35 on the surface of the sheet 31 are also softened while the craters 6 are being formed, and in addition they are entrained during deformation of the sheet 31. The extent to which the fibers 34 are entrained is a function of various operating conditions, and in particular on the heating temperature, the pressure that may have been exerted to apply the fibers 35 onto the sheet 31, the length of the fibers 35, the proportion of non-thermoplastic fibers in the fiber mix, the difference between the softening temperature of the fibers 35 and that of the sheet 31. . . . . Thus, while the blisters are being created, a more or less large quantity of fibers 35 remains bonded to the sidewalls of the blister, such that after bursting and formation of the crater 6, said fibers cover the sidewalls 7 and 7' of said crater 6, regardless of the angle of inclination $\alpha$ taken up by the sidewall, and as can be seen in FIG. 5. In particular, when residual bonding takes place between two zones of discontinuity in the form of filamentary elements 12, fibers 35 can be bonded to said filamentary elements 12, thereby improving the covering power of the fibers on the smooth outside face of the sheet 31.

It is preferable to locate a device 46 for spraying adhesive 37 on the path of the thermoplastic sheet 31 upstream from the device 34 for spraying on the fibers 35, with the adhesive being deposited in uniform and small quantity over the entire top face of the sheet 31. The device may be a melt-blown type device that blows on adhesive 47 in the form of an adhesive thermoplastic resin.

The adhesive must be applied in a quantity sufficient for ensuring that the fibers hold to one another and to the sheet while being sufficiently small to avoid spoiling the flexibility of the material of the invention. This quantity is also a function of the quantity of fibers 35 deposited on the sheet 31; the preferred range of 0.2 $g/m^2$ to 5 $g/m^2$ for the adhesive corresponds to a range 2 $g/m^2$ to 20 $g/m^2$ for the fibers.

It is also possible to disperse the fibers on a sheet that has already been perforated. Under such circumstances, the fibers must be dispersed on the face of the sheet which does not include craters and the fibers must be at a temperature such that on cooling they adhere to one another and to the smooth zones of the sheet. Such conditions are obtained by extruding the fibers directly above the continuously running sheet and projecting said fibers onto the sheet while they are still at a temperature greater than the melting temperature of the thermoplastic substance from which they are made.

Under such circumstances, it is also preferable to pre-coat the face of the sheet onto which the fibers are projected with an adhesive. The adhesive may be a thermoplastic adhesive resin, for example, that reacts at the temperature at which the fibers come into contact with the sheet.

In the above example, only the face of the sheet corresponding to the sidewalls of the craters 6 has a fiber covering. The invention is not limited thereto. Material having two fibrous faces can be made by a first passage through the installation of FIG. 4 followed by fibers being blown onto the other face using the method of direct extrusion onto the sheet.

Finally, in another version, it is possible to start with a fibrous web that has already been made, and to extrude the thermoplastic sheet directly onto said web, prior to passing the assembly comprising the fiber web and the extruded sheet over the rotary drum of the above-described installation in order to make the craters.

I claim:

1. A perforated sheet made out of a substance that is impervious to liquids, said perforated sheet comprising a plurality of craters, each having a base in a plane of an outside face of the sheet, an apex remote from said plane, and a sidewall which is inclined from the base to the apex of the crater, wherein the base of each crater has a peripheral shape including at least one zone of inward contraction along its peripheral curve, the sidewall having angles of inclination relative to the perpendicular to the plane of the outside face of the sheet varying between positive values and negative values, said negative values of said angles presented in the zone of inward contraction of the peripheral curve.

2. A sheet according to claim 1, wherein the peripheral shape of the base of the crater includes a plurality of curved geometrical shapes partially overlapping one another, and wherein each zone of inward contraction of the peripheral curve corresponds to the junction between overlapping shapes.

3. A sheet according to claim 2, wherein the base of each crater has a curved outline with a longitudinal axis of symmetry that is resulted from partially overlapping an ellipse with at least one circle whose center lies on the longitudinal axis of the ellipse.

4. A sheet according to claim 2, wherein the base of each crater has a curved outline with a longitudinal axis of symmetry, that is resulted from partially overlapping an ellipse with two circles that are disposed at opposite ends of the ellipse, the base of each crater thus including four zones of inward contraction of the peripheral curve corresponding to the junctions between the substantially elliptical central portion and the two substantially circular end portions.

5. A sheet according to claim 3, wherein the length of each crater along its longitudinal axis of symmetry is in the range of 2.6 mm to 4 mm, and the diameter of the circle is in the range of 0.6 mm to 3 mm.

6. A sheet according to claim 3, including a plurality of types of crater alignment, the craters in the same type of alignment being regularly aligned along a common longitudinal axis of symmetry, with alignments of the same type having the same general direction.

7. A sheet according to claim 6, having four types of alignment, whose general directions are mutually angularly offset through angles of 45°.

8. A sheet according to claim 1, wherein some craters include, in a given zone of inward contraction of the peripheral curve, fibril elements forming spacers between the sidewalls that face each other in said zone of inward contraction.

9. A composite plane material comprising a perforated thermoplastic sheet having a plurality of craters, each having a base in a plane of an outside face of the sheet, an apex remote from said plane, and a sidewall which is inclined from the base to the apex of the crater; wherein the base of each crater has a peripheral shape including at least one zone of inward contraction along its peripheral curve, the sidewall having angles of inclination relative to the perpendicular to the plane of the outside face of the sheet varying between positive values and negative values, said negative values of said angles presented in the zone of inward contraction of the peripheral curve, and fibers which are bonded to one another and to the sheet in substantially continuous manner and which cover at least the outside face of said sheet.

10. A composite plane material according to claim 9, wherein the fibers are also bonded to and cover the sidwalls of the craters.

11. A composite plane material according to claim 9, wherein some craters include, in a given zone of inward contraction of the peripheral curve, fibril elements forming spacers between the sidewalls that face each other in said zone of inward contraction, and the majority of the fibers are thermoplastic, the fibers covering over the fibril elements forming spacers between the facing sidewalls in certain zones of inward contraction of the peripheral curve in the craters.

12. A method of manufacturing a fibrous composite plane material comprising the steps of:

a) dispersing a web of fibers, the majority of which are thermoplastic fibers, on a thermoplastic sheet;

b) presenting the sheet and fiber assembly thus obtained on a surface that is provided with orifices, the peripheral shape of each orifice being resulted from partially overlapping a plurality of curved geometrical shapes; and c) heating said assembly to a temperature closes to the softening temperature of the thermoplastic substances constituting the fibers and the sheet while simultaneously establishing suction through the orifices so as to obtain craters by bursting the sheet where the sheet overlies the orifices, each crater having a base of a peripheral shape whose peripheral curve includes at least one zone of inward contraction round the periphery of each crater, a sidewall of the crater having angles of inclination relative to the perpendicular to the plane of a smooth outside face of the sheet, said inclination angles varying angles between positive values and negative values, said negative value angles presented in the zone of inward contraction of the peripheral curve.

13. A method according to claim 12, wherein the surface, on which the sheet and fiber assembly is presented, is constituted by the peripheral surface of a rotary drum fitted with an internal suction system.

14. A method according to claim 12, including a prior step of pre-coating the smooth outside face of the sheet on which the fibers are dispersed in adhesive.

15. A method according to claim 14, wherein the adhesive is pre-coated by the melt-blown technique at a rate of 0.2 g/m² to 5 g/m².

16. A method according to claim 12, wherein the step (a) is replaced by extruding a thermoplastic sheet onto a web of fibers.

17. A method of manufacturing a fibrous composite plane material, comprising the steps of presenting a perforated thermoplastic sheet having a plurality of craters, each having a base in a plane of a smooth outside face of the sheet, an apex remote from said plane, and a sidewall which is inclined from the base to the apex of the crater, wherein the base of each crater has a peripheral shape including at least one zone of inward contraction along its peripheral curve, the sidewall having angles of inclination relative to the perpendicular to the plane of the outside face of the sheet, said angles varying between positive values and negative values with said negative value angles presented in the zone of inward contraction of the peripheral curve, and dispersing a web of thermoplastic fibers on the perforated thermoplastic sheet, said fiber dispersing being performed over at least the smooth outside face of the sheet at a temperature which is sufficient for the fibers to adhere naturally to the surface of the sheet after the sheet has cooled down such that the fibers are bonded to one another and to the sheet in substantially continuous manner and cover at least the smooth outside face of said sheet.

* * * * *